United States Patent
Ransing et al.

(10) Patent No.: US 7,440,928 B2
(45) Date of Patent: Oct. 21, 2008

(54) DIAGNOSTIC APPARATUS

(75) Inventors: Rajesh S. Ransing, Swansea (GB); Meghana R. Ransing, Swansea (GB); Roland W. Lewis, Swansea (GB)

(73) Assignee: MetaCause Solutions Ltd. (GB)

( * ) Notice: Subject to any disclaimer, the term of this patent is extended or adjusted under 35 U.S.C. 154(b) by 0 days.

(21) Appl. No.: 10/484,673

(22) PCT Filed: Aug. 15, 2002

(86) PCT No.: PCT/GB02/03805

§ 371 (c)(1), (2), (4) Date: Jul. 21, 2004

(87) PCT Pub. No.: WO03/015628

PCT Pub. Date: Feb. 27, 2003

(65) Prior Publication Data

US 2004/0249777 A1 Dec. 9, 2004

(30) Foreign Application Priority Data

Aug. 15, 2001 (GB) .................................. 0120009.6

(51) Int. Cl.
*G06F 15/18* (2006.01)

(52) U.S. Cl. ..................... 706/14; 706/12; 706/45; 700/95; 700/110

(58) Field of Classification Search ........ 706/1, 706/14, 18, 20, 21, 45–48, 50, 52, 61, 903, 706/906, 914, 12; 700/95, 96, 108–110, 700/115, 116; 714/25, 26, 48
See application file for complete search history.

(56) References Cited

U.S. PATENT DOCUMENTS 5,442,562 A * 8/1995 Hopkins et al. ............. 700/108
6,076,083 A * 6/2000 Baker .......................... 706/52

(Continued)

OTHER PUBLICATIONS

"FEM-Based Neural-Network Approach to Nonlinear Modeling with Application to Longitudinal Vehicle Dynamics Control" IEEE Transaction on Neural Network, vol. 10, No. 4, 1999, J. Kalkkuhl et al.
"Eight More Classic Machine Learning Algorithms", 2001, Andrew W. Moore, Carnegie Mellon University.

*Primary Examiner*—David Vincent
*Assistant Examiner*—Omar F Fernandez Rivas
(74) *Attorney, Agent, or Firm*—Waddey & Patterson, P.C.; Emily A. Shouse (57) ABSTRACT

Apparatus and method for determining a likely cause or the likelihood of the occurrence of a cause of one or more effects, in which training data relating to previously identified relationships between one or more causes and one or more effects is used to learn the cause and effect relationship. A number of primary and secondary reference points are chosen in the input space created by belief values representing the strength of effect. A function representing the cause and effects relationship and a weight value is associated with each reference point. Weight values associated with primary reference points are considered as independent variables (primary weight values) and other weight values, which are associated with secondary reference points (secondary weight values), depend on one or more primary weight values. Belief value in the occurrence of likely causes of one or more given effects can be determined using this method or apparatus.

19 Claims, 5 Drawing Sheets

U.S. PATENT DOCUMENTS 6,199,018 B1 * 3/2001 Quist et al. .................. 702/34
6,327,581 B1 * 12/2001 Platt ........................... 706/12
6,745,157 B1 * 6/2004 Weiss et al. ................... 703/2
2001/0013027 A1 * 8/2001 Akkiraju et al. ............. 706/21

* cited by examiner

DIAGNOSTIC APPARATUS

This invention relates to an apparatus and method for assisting in diagnosing cause and effect in many different circumstances throughout various different disciplines.

In recent times, various disciplines, including the manufacturing industry and at least some branches of the medical field, have come under increasing pressure to increase yield, productivity and profits (or reduce costs or overheads). As such, there is an increasing need to reduce costs and reach the required result as quickly as possible, for example, in the manufacturing industry, the required result may be the manufacture of a batch of products which are all of optimum quality, and in a branch of the medical field, the required result might be the correct diagnosis of a complaint or disease in a patient (i.e. in both cases, to get it "right first time").

In the case of the manufacturing industry, manufactured products are usually tested for quality, and sub-standard units are rejected. When a unit or set of units is rejected, the fault or faults are generally noted and it is highly desirable to establish the reason for the occurrence of the faults so that any problems can be rectified and the chances of manufacturing sub-standard products thereafter can be minimised. Such diagnosis is usually performed by experts in the field, who have acquired a fundamental understanding over the years of cause and effect relationships, which often influences the occurrence of rejected product units. Similarly, a patient will usually visit a general practitioner with one or more symptoms, from a description of which the doctor must try and diagnose the problem, based on current medical knowledge and his experience in the field. Thus, in general, cause and effect relationships are learned by experts in a particular field and applied in the diagnosis of problems when they occur in that field.

However, this manual diagnosis procedure is time consuming and, therefore, increases costs and reduces productivity and yield. Further, when an expert leaves a particular place of employment, his expertise is also lost to the employer.

Figure 1A:
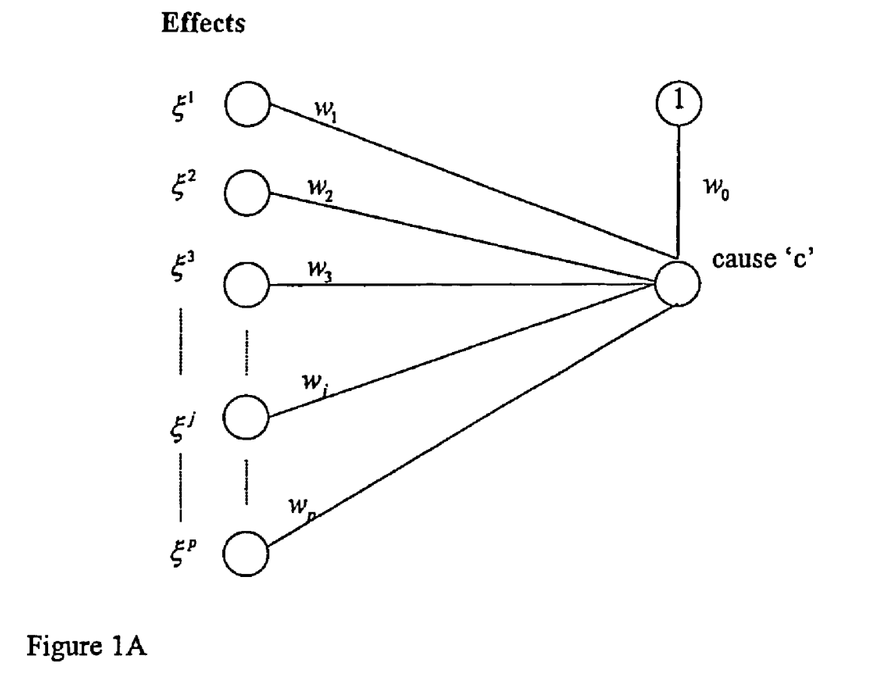
FIGS. 1A and 1B is a schematic illustration of a manifestation cause relationship.
Figure 1B:
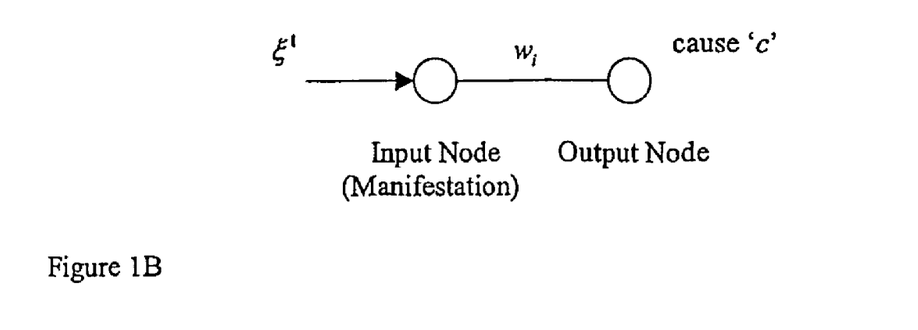

Attempts have been made in the past to relate belief values, representing the strength of an effect, to a belief value which quantifies the extent of occurrence of an associated cause, using either multivariate regression analysis methods or neural network related methods. If the belief values in 'p' manifestations associated with a cause 'c' are represented by 'p' variables $\xi^1, \xi^2, \xi^3, \ldots \xi^p$ (as shown in FIG. 1), then using the multivariate linear regression analysis method [1] or single layered feed forward neural network method [2], the belief value, which quantifies the extent of occurrence of cause 'c', is given by the following equation:

$$\text{Belief in cause} = w_0 + w_1\xi^1 + w_2\xi^2 + w_3\xi^3 + \ldots + w_j\xi^j + \ldots + w_p\xi^p \quad (1)$$

where $w_j$, $j=0$ to $p$ are referred to as either regression coefficients (in a regression analysis context) or weights (in a neural network context). These coefficients, or weights, generally being considered as independent variables, are mostly determined using least square minimisation techniques. This is achieved by comparing the belief value in the cause calculated by equation (1) with a previously known value for the same inputs.

Multi-layered feed forward neural network techniques, including radial basis functions [2], and also a range of methods proposed in the family of intrinsically linear, multivariate regression analysis [1], generalise equation (1) in the following way:

$$\text{Belief in cause} = w_0 + w_1 z_1 + w_2 z_2 + w_3 z_3 + \ldots + w_i z_i + \ldots + w_m z_m \quad (2)$$

where $z_i$ ($i=1$ to $m$) represents a function of $\xi_j$, ($j=1$ to $p$)

Different methods and apparatuses may use different functions ($z_i$) ranging from simple linear polynomials to higher order, non-linear polynomials, logarithmic or exponential functions.

Although, these methods have been employed to associate belief values in causes to belief values in effects, the methods have two major limitations:
1. Physical interpretation can not be assigned to either weights $w_i$ or functions $z_i$, as given in equation (2), which makes it very difficult to gain any physical insight into the cause and effect relationship.
2. The number and the type of function used to define $z_i$ are not unique and are determined by a trial and error method.

These limitations constrain the applicability of existing methods to relate belief values, which quantify the occurrence of a cause, with belief values representing strength of effects.

The inventors have now devised an arrangement that overcomes the limitations/problems outlined above and seeks to provide a generic tool to relate belief values in causes and effects for use in many different fields, and industries, for diagnosing problems occurring therein.

Thus, in accordance with the first aspect of the present invention, there is provided apparatus for determining a likelihood of occurrence of a cause of one or more effects, the apparatus comprising means for receiving and/or accessing training data relating to previously-identified relationships between one or more causes and one or more effect means, for defining one or more functions representative of said relationships, said function(s) being in the form of polynomials which define quantified mappings between said one or more causes and one or more effects, each of said polynomials being associated with each of a plurality of respective reference points, at least some of which have a weight value assigned thereto, at least one of said weight values being an independent variable ("primary weight") and at least one of said weight values being dependent on one or more of said primary weights ("secondary weight"), and means for determining a likelihood of occurrence of one or more causes of one or more given effects using said mappings.

Also in accordance with the first aspect of the present invention, there is provided a method of determining a likelihood of occurrence of a cause of one or more effects, the method comprising the steps of receiving and/or accessing quantifying data relating to previously-identified relationships between one or more causes and one or more effects, defining one or more functions representative of said relationships, said function(s) being in the form of polynomials which define quantified mappings between said one or more causes and one or more effects, each said polynomials being associated with each of a plurality of respective reference points, at least some of which have a weight value assigned thereto, at least one of said weight values being an independent variable ("primary weight") and at least one of said weight values being dependent on at least one of said primary weights ("secondary weight"), and determining a likelihood of occurrence of one or more causes of one or more given effects using said mappings.

Thus, the present invention not only provides a method and apparatus for automatically providing diagnostic information relating to one or more likely causes of one or more given manifestations or effects, thereby reducing the input required by expert personnel once sufficient training data has been entered, where human input can otherwise be time consuming and is, of course, prone to error as it is generally based only on the opinion of very few experienced personnel; but also significantly reduces the number of independent weight values required to facilitate the diagnostic process, thereby reducing the quantity of training data required to a practical level when a large number of effects or manifestations of a cause are involved.

The present invention provides a method and apparatus for calculating a belief value which quantifies the extent of occurrence of a cause, given belief values which quantify the occurrence, or non-occurrence, of associated affects of the cause. Examples of effects of a cause, which are indicative but certainly not exhaustive, are "symptoms" shown by patients in the medical domain, "defects" occurring in components in manufacturing industry or "effects" as generally meant in any "cause and effect" diagram.

The belief value quantifying the occurrence, or non-occurrence, of an effect associated with a particular cause is preferably normalised between +1 to −1 or 1 to 0 respectively. This belief value may also be interpreted as being the strength of the effect. The belief value, which quantifies the extent of occurrence of the cause under consideration, is preferably also normalised from zero to unity or −1 to +1 to represent non-occurrence and occurrence, respectively.

The present invention also allows a meaningful physical interpretation to be assigned to each and every said weight value (primary and secondary weights) in the sense that a weight value at a position described by belief values, which represent the strength of associated manifestation, is nothing but the output value i.e. a belief value representing the extent of occurrence of the cause given the strengths of the associated effects.

In a preferred embodiment of the present invention, the apparatus comprises a means of producing a multi-dimensional hyper-surface representing belief values in the occurrence/non-occurrence of a cause. The number of dimensions of the hyper-surface is equal to the number of input nodes representing the effects of a cause. The order of the hyper-surface along each dimension is determined by the order of the polynomial, preferably a Lagrange Interpolation Polynomial, used along the said dimension. The first order (or linear) Lagrange Interpolation Polynomial is defined by two reference points. Second order or quadratic Lagrange Interpolation Polynomials require three reference points. Similarly, an $n^{th}$ ordered Lagrange Interpolation Polynomial will require (n+1) reference points along the given dimension. The apparatus or method of calculating reference points including primary reference points and then associating a weight value along with the Lagrange Interpolation Polynomial at each reference point is described in more detail below.

The training data is preferably made up of one or more training files, the or each file comprising an input vector, storing belief values representing strengths of all associated effects, and its corresponding desired output vector, storing belief values, which quantify the extent of occurrence of the corresponding cause.

An embodiment of the present invention will now be described by way of example only, followed by sample numerical calculation and with reference to the accompanying drawings, in which.

In order to facilitate the description of an exemplary embodiment of the present invention, a number of general one-dimensional cause and effect relationships associating belief values (based on the network illustrated in FIG. 1B) will first be illustrated. FIGS. 2A-2E, show possible examples of the variation in belief values, representing the extent of occurrence of cause (output value), with respect to the belief values, representing the strength of one of the associated effect.

Figure 2A:
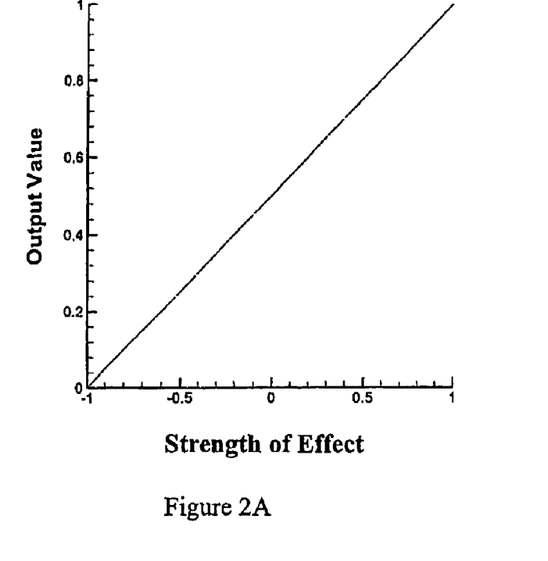
FIGS. 2A to 2E are graphical representations of some general one-dimensional cause and effect relationships.

Referring to FIG. 2A of the drawings, a linear variation in belief values is shown, in which when the belief value representing the strength of effect is at its minimum, the belief value representing the extent of occurrence of the related cause is also at its minimum. As the strength of effect increases, the belief value in the occurrence of cause also linearly increases.

Figure 2B:
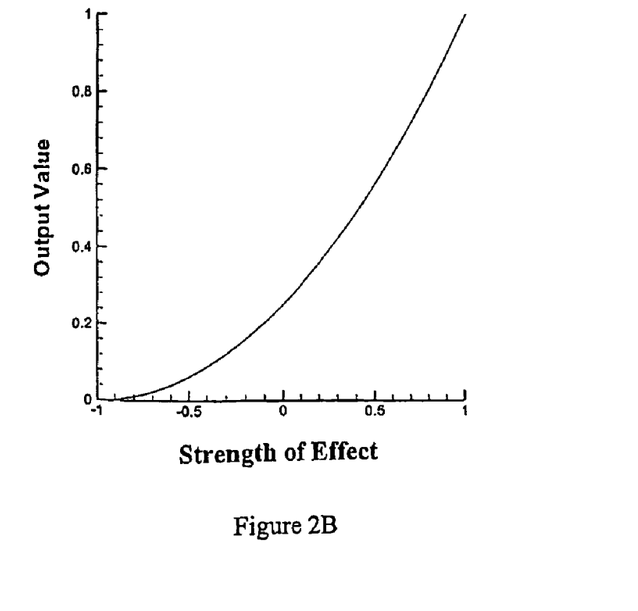

Referring to FIG. 2B of the drawings, a quadratic variation of cause and effect is shown in which when the belief value representing the strength of the effect is at its minimum, then the belief value in the occurrence of the related cause is also at its minimum. As the strength of the effect starts to increase, the belief value in the occurrence of the corresponding cause also starts to slowly increase. As the strength of the effect increases to about half of its maximum value, so the belief value in the occurrence of the cause suddenly increases and reaches its maximum value when the strength of the effect reaches its maximum value.

Figure 2C:
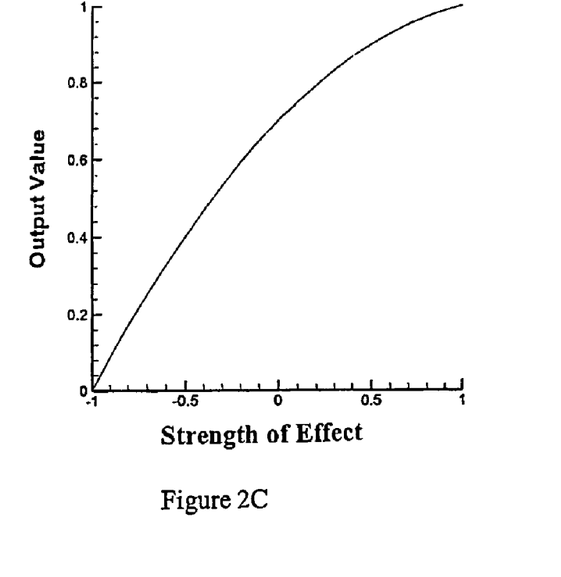

Referring to FIG. 2C of the drawings, a quadratic variation of cause and effect is shown which, when the belief value representing the strength of the effect is at its minimum, then the belief value in the occurrence of the related cause is also at its minimum. As the strength of the effect starts to increase, the belief value in the occurrence of the cause quickly starts to increase. When the strength of the effect is around half of its maximum value, the rate of increase in the belief value of the occurrence of the related cause slows down and reaches its maximum value when the strength of the effect also reaches its maximum value.

Figure 2D:
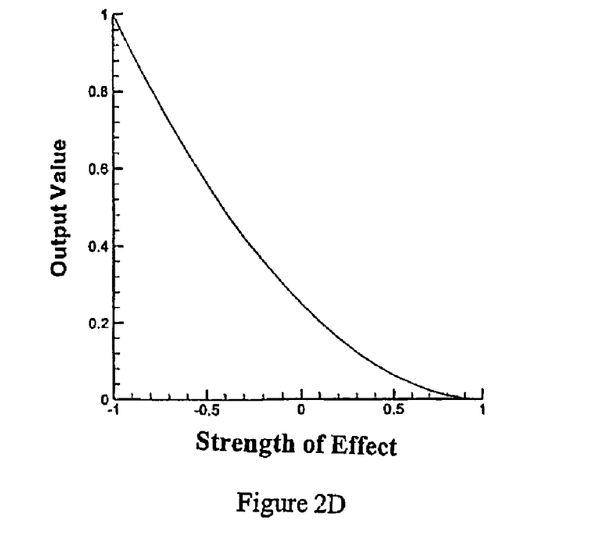

Referring to FIG. 2D of the drawings, a quadratic variation of cause and effect is shown in which when the belief value representing the strength of the effect is at its minimum, then the belief value in the occurrence of the related cause is at its maximum. As the strength of the effect starts to increase, there is a quick reduction in the belief value in the occurrence of the cause. As the strength of the effect increases to about half of its maximum value, the belief value in the occurrence of the cause slowly decreases and reaches its minimum value when the strength of the effect is at its maximum.

Figure 2E:
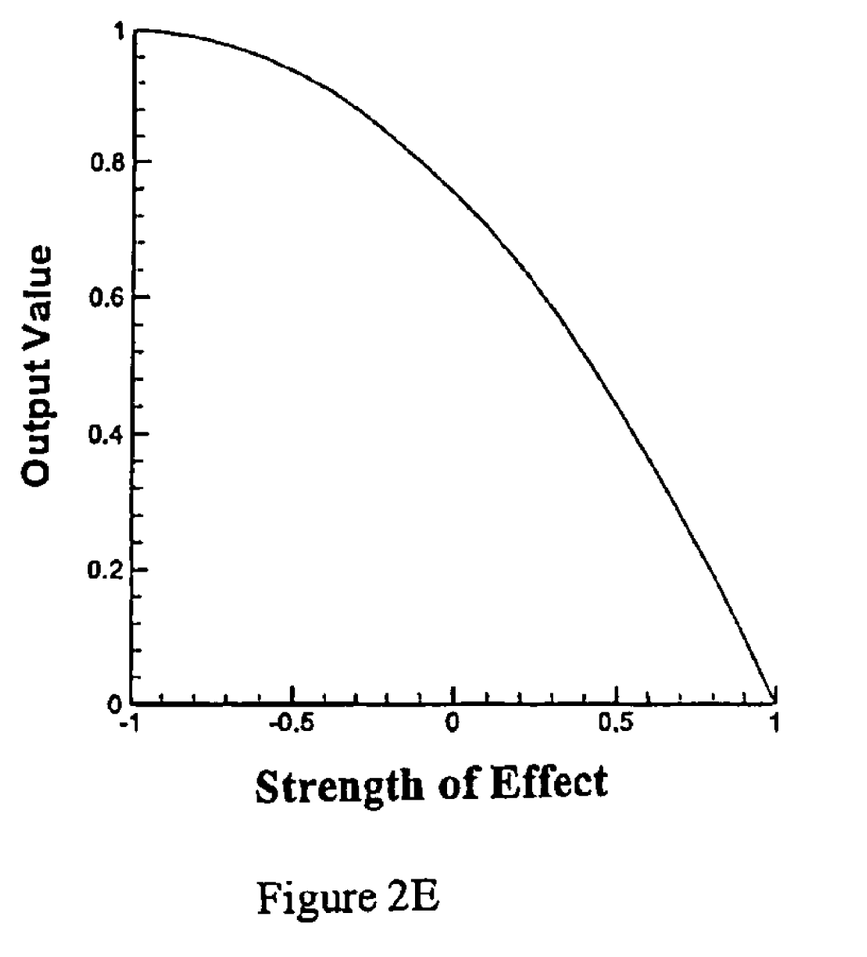
Figure 3:
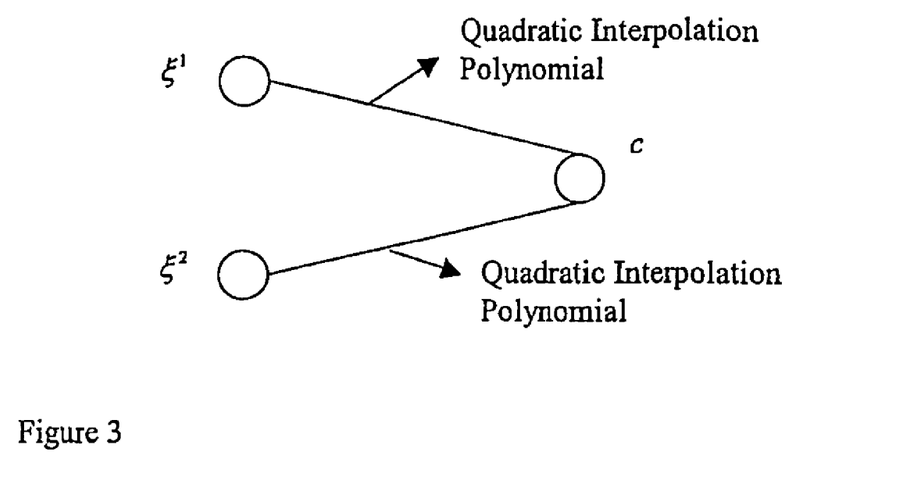
FIG. 3 is a schematic diagram illustrating a two effect—one cause relationship.

Referring to FIG. 2E of the drawings, a quadratic variation of cause and effect is shown in which when the belief value representing the strength of the effect is at its minimum, then the belief value in the occurrence of the related cause is at its maximum. As the strength of the effect starts increasing, the belief value in the occurrence of the cause slowly starts to decrease. When the strength of the effect reaches around half of its maximum value, the belief value in the occurrence of the cause starts to decrease quickly and reaches its minimum when the strength of the effect is at its maximum.

It is an object of the present invention to provide a diagnostic arrangement, which not only "learns" from examples, but also quantifies the cause and effect relationship, which may be described in this exemplary embodiment of the invention by a decision hyper-surface constructed by combining Lagrange Interpolation Polynomials. Two reference points associated with two Lagrange Interpolation Polynomials and two weight values are required to describe a linear variation in the belief values as shown in FIG. 2A. Similarly, three reference points along with three Lagrange Interpolation Polynomials and weight values are required to describe one dimensional quadratic belief variation as shown in FIGS. 2B-2E. The learning function of the apparatus is equivalent to finding a multi-dimensional hyper-surface, describing the said belief variation, which provides a best fit to the training data.

Thus, an exemplary embodiment of the invention provides a method for calculating a belief value, which quantifies the extent of occurrence of a cause, given belief values, which quantify the occurrence or non-occurrence of associated effects of the cause. Examples of effects of a cause are, but not limited to, "symptoms" shown by patients in the medical domain, "defects" occurring in components in manufacturing industry or "effects" as generally meant in any "cause and effect" diagram. The belief value $\xi$, which quantifies the occurrence or non-occurrence of an effect associated with a particular cause is normalised between +1 to −1 respectively. This belief value is also interpreted to represent the strength of the effect. The belief value, which quantifies the extent of occurrence of the cause under consideration is also normalised from zero to unity, to represent non-occurrence and occurrence of the said cause respectively.

The relationship between the belief value, representing the strength of the effect, and the belief value, representing the extent of occurrence of the cause, is assumed to be either linear, quadratic, cubic and so on. The order of the relationship (e.g. one for linear, two for quadratic, three for cubic etc.) can either be given or calculated iteratively starting from one. To define an $n^{th}$ order relationship along one-dimension, (n+1) reference points, equidistant between −1 to +1, are chosen. (If the location of the reference points is not equidistant, these reference points are mapped on to another set of equidistant reference points.) For each reference point 'i', a one dimensional Lagrange Interpolation Polynomial is constructed based on the following formula:

$$l_i(\xi) = l_k^n(\xi) = \frac{\xi - \xi_0}{\xi_k - \xi_0} * \frac{\xi - \xi_1}{\xi_k - \xi_1} * \frac{\xi - \xi_2}{\xi_k - \xi_2} * \ldots * \frac{\xi - \xi_{k-1}}{\xi_k - \xi_{k-1}} * \frac{\xi - \xi_{k+1}}{\xi_k - \xi_{k+1}} * \ldots * \frac{\xi - \xi_n}{\xi_k - \xi_n} \quad (3)$$

where,
- n: order of the Lagrange Interpolation Polynomial (one for linear, two for quadratic, etc.)
- k: A reference point at which the one-dimensional Lagrange Interpolation Polynomial $l_k^n(\xi)$ is constructed. k ranges from 0 to n.
- i: Ranges from one to total number of reference points i.e. (n+1).

$\xi_0, \xi_1, \xi_2 \ldots \xi_n$ are (n+1) equidistant reference points from $\xi_0 = -1$ to $\xi_n = +1$ with (n+1) corresponding Lagrange Interpolation Polynomials as given by equation (3). The variable $\xi$, which stores the belief value representing the strength of the corresponding effect, ranges from −1 to +1. For a "single effect—cause relationship", the Lagrange Interpolation Polynomial is one-dimensional and the reference points are drawn along this dimension. If the number of associated manifestations for a given cause is 'p', the Lagrange Interpolation Polynomial at a reference point 'i' will be 'p' dimensional and is given by the following equation:

$$l_i(\xi^1, \xi^2, \xi^3, \ldots \xi^j, \xi^p) = l_{k_1}^{n_1}(\xi^1) * l_{k_2}^{n_2}(\xi^2) * \ldots * l_{k_j}^{n_j}(\xi^j) * \ldots * l_{k_p}^{n_p}(\xi^p) \quad (4)$$

where, $$l_{k_j}^{n_j}(\xi^j) = \frac{\xi^j - \xi_0^j}{\xi_{k_j}^j - \xi_0^j} * \frac{\xi^j - \xi_1^j}{\xi_{k_j}^j - \xi_1^j} * \frac{\xi^j - \xi_2^j}{\xi_{k_j}^j - \xi_2^j} * \ldots * \frac{\xi^j - \xi_{k_j-1}^j}{\xi_{k_j}^j - \xi_{k_j-1}^j} * \frac{\xi^j - \xi_{k_j+1}^j}{\xi_{k_j}^j - \xi_{k_j+1}^j} * \ldots * \frac{\xi^j - \xi_{n_j}^j}{\xi_{k_j}^j - \xi_{n_j}^j} \quad (5)$$

- $n_j$: Order of one dimensional Lagrange Interpolation Polynomial ($l_{k_j}^{n_j}(\xi^j)$) corresponding to $j^{th}$ dimension that represents the relationship between $j^{th}$ manifestation and the cause under consideration.
- $k_j$: Reference point along $j^{th}$ dimension, at which the one dimensional Lagrange Interpolation Polynomial $l_{k_j}^{n_j}(\xi^j)$ is evaluated. ($k_j$ ranges from 0 to $n_j$.)
- $\xi_0^j, \xi_1^j, \xi_2^j, \ldots, \xi_{n_j}^j$ are ($n_j$+1) reference points along the $j^{th}$ dimension.

These are the primary reference points as they lie along the $j^{th}$ dimensional axis.

i: Ranges from one to total number of reference points 'q'.

As $k_j$ independently varies from 0 to $n_j$ for each Lagrange Interpolation Polynomial, $$q = (n_1+1) * (n_2+1) * (n_3+1) * \ldots * (n_j+1) * \ldots * (n_p+1) \quad (6)$$

Thus, the co-ordinates for a reference point 'i', corresponding to each dimension, are given as $(k_1, k_2, \ldots, k_j, \ldots, k_p)$.

The reference points, which lie along the dimensional axes, are special points and are referred to as "primary reference points". In terms of co-ordinates, a reference point is along the dimensional axis if one and only one of its co-ordinates ($k_j$) has a non-zero value and all other co-ordinates is zero.

A weight variable with values constrained between zero and unity is associated with each reference point. Therefore, the total number of weights is the same as the total number of reference points 'q'. A weight value at a reference point, in the context of this invention, is considered to be representative of the belief value in the cause. Weights corresponding to primary reference points are chosen as primary or independent weights and the remaining weights—referred to as secondary weights—are dependent on, and expressed as a linear combination of primary weights. This dramatically reduces the number of unknown variables within the network, thereby reducing the amount of training data required to a practical level as compared with conventional techniques. For example, for a 'p' dimensional problem, the number of primary weights is $$\left[\left(\sum_{j=1}^{p} n_j + 1\right) - (p-1)\right]. \quad (7)$$

During the learning or training process, the optimal values for primary weights (constrained between zero and one) and coefficients used in the linear combination expression are determined based on any user defined method including generally available optimisation principles. The secondary weights are also constrained between zero and one.

The belief value in the occurrence of a cause, based on the known belief values ($\xi^j$, j=1 to p) quantifying the strength of 'p' associated effects, is given by the following equation:

The belief value in the cause $= \sum_{i=1}^{q} w_i l_i(\xi^1, \xi^2, \ldots, \xi^p)$ (8)

where,
q: Total number of reference points.
$l_i(\xi^1, \xi^2, \ldots, \xi^p)$ is given by equation (4).
$w_i$: Weight variable associated with the $i^{th}$ reference point.

In an embodiment of the present invention, a secondary weight is defined as a linear combination of primary weights. However, the following particular cases of linear combination may also be used in other preferred embodiments of the present invention.
1. A secondary weight value associated with a reference point is a linear combination of those primary weight values, which are associated with primary reference points corresponding to the co-ordinates of the said reference point.
2. A secondary weight value associated with a reference point is a constant multiplied by the average of primary weight values, which are associated with primary reference points corresponding to the co-ordinates of the said reference point.

A NUMERICAL EXAMPLE OF AN EXEMPLARY EMBODIMENT OF THE PRESENT INVENTION

Two effects, $\xi^1$ and $\xi^2$, are associated with a cause c. Therefore, two-dimensional Lagrange Interpolation Polynomials $l_i(\xi^1, \xi^2)$ will be used for defining the hypersurface. Quadratic relationship is assumed between belief values for the effect $\xi^1$ and the cause c, and also for the effect $\xi^2$ and the cause c.

For this example, the belief value in the occurrence of cause c is calculated for a belief value in the first effect $\xi^1$ equal to 0.5 and a belief value in the second effect $\xi^2$ equal to $-0.5$.

Figure 4:
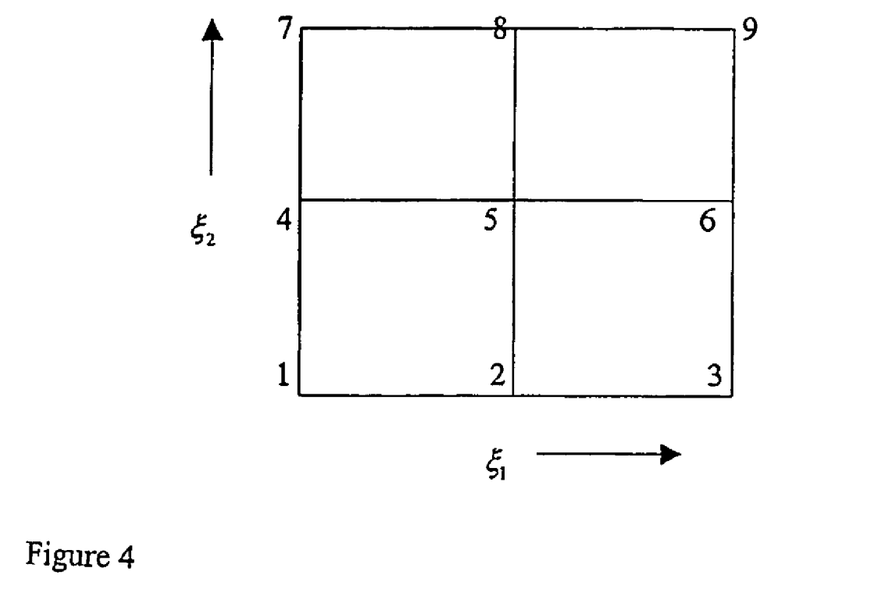
FIG. 4 is a schematic diagram illustrating a two dimensional space describing $\xi^1$ and $\xi^2$ axes.

Numbers 1 to 9 in FIG. 4 denote equidistant reference points. As a result of quadratic relationship, ($\xi^1$ and $\xi^2$ equal to 2) three equidistant reference points are used along each dimension. Using equation (6), it can be seen that the total number of reference points is 9.

Using equation (7), it can be seen that total number of primary reference points is 5. These points are also indicated in the following table (Table 1), which shows the co-ordinates of all nine reference points in various forms.

TABLE 1

| Reference Points ($i = 1$ to q) | Coordinates in terms of $k_j$ | Coordinates in terms of $\xi^j$ | Coordinates in terms of actual numerical values for $\xi$'s |
|---|---|---|---|
| 1. | (0, 0) Primary | $(\xi_0^1, \xi_0^2)$ | $(-1, -1)$ |
| 2. | (1, 0) Primary | $(\xi_1^1, \xi_0^2)$ | $(0, -1)$ |
| 3. | (2, 0) Primary | $(\xi_2^1, \xi_0^2)$ | $(+1, -1)$ |
| 4. | (0, 1) Primary | $(\xi_0^1, \xi_1^2)$ | $(-1, 0)$ |
| 5. | (1, 1) Secondary | $(\xi_1^1, \xi_1^2)$ | $(0, 0)$ |
| 6. | (2, 1) Secondary | $(\xi_2^1, \xi_1^2)$ | $(1, 0)$ |
| 7. | (0, 2) Primary | $(\xi_0^1, \xi_2^2)$ | $(-1, +1)$ |
| 8. | (1, 2) Secondary | $(\xi_1^1, \xi_2^2)$ | $(0, +1)$ |
| 9. | (2, 2) Secondary | $(\xi_2^1, \xi_2^2)$ | $(+1, +1)$ |

Weights associated with primary reference points 1, 2, 3, 4 and 7 are primary weights and are also independent parameters. The secondary weight values at locations 5, 6, 8 and 9 are expressed as linear combination of primary weights and in particular $w_5 = \frac{C(w_2 + w_4)}{2}$ (9)

$w_6 = \frac{C(w_3 + w_4)}{2}$ (10)

$w_8 = \frac{C(w_2 + w_7)}{2}$ and (11)

$w_9 = \frac{C(w_3 + w_7)}{2}.$ (12)

Thus, the independent parameters which are passed on to the optimisation algorithm during a learning process are $w_1$, $w_2$, $w_3$, $w_4$, $w_7$ and constant C.

The belief value, in the extent of the occurrence of cause, for a given belief value $\xi^1$ equal to 0.5 (representing the strength of effect $\xi^1$) and a given belief value $\xi^2$ equal to $-0.5$ (representing the strength of effect $\xi^2$) is calculated as:

$$\text{The belief value in the occurrence of cause} = \sum_{i=1}^{9} w_i l_i(0.5, -0.5)$$

Using equations (4) and (5), Lagrange Interpolation Polynomials are constructed and then evaluated at (0.5, $-0.5$) at all reference points.

Lagrange Interpolation Polynomial for reference point 1:

$$l_1(\xi^1, \xi^2) = l_0^2(\xi^1) * l_0^2(\xi^2)$$
$$= \left(\frac{\xi^1 - \xi_1^1}{\xi_0^1 - \xi_1^1} * \frac{\xi^1 - \xi_2^1}{\xi_0^1 - \xi_2^1}\right) * \left(\frac{\xi^2 - \xi_1^2}{\xi_0^2 - \xi_1^2} * \frac{\xi^2 - \xi_2^2}{\xi_0^2 - \xi_2^2}\right)$$
$$= \frac{1}{4}(\xi^1)(\xi^1 - 1)(\xi^2)(\xi^2 - 1)$$

$l_1(0.5, -0.5) = -0.0469$

Lagrange Interpolation Polynomial for reference point 2:

$$l_2(\xi^1, \xi^2) = l_1^2(\xi^1) * l_0^2(\xi^2)$$
$$= \left(\frac{\xi^1 - \xi_0^1}{\xi_1^1 - \xi_0^1} * \frac{\xi^1 - \xi_2^1}{\xi_1^1 - \xi_2^1}\right) * \left(\frac{\xi^2 - \xi_1^2}{\xi_0^2 - \xi_1^2} * \frac{\xi^2 - \xi_2^2}{\xi_0^2 - \xi_2^2}\right)$$
$$= -\frac{1}{2}(\xi^1 + 1)(\xi^1 - 1)(\xi^2)(\xi^2 - 1)$$

$l_2(0.5, -0.5) = 0.2813$

Lagrange Interpolation Polynomial for reference point 3:

$$l_3(\xi^1, \xi^2) = l_2^2(\xi^1) * l_0^2(\xi^2)$$
$$= \left(\frac{\xi^1 - \xi_0^1}{\xi_2^1 - \xi_0^1} * \frac{\xi^1 - \xi_1^1}{\xi_2^1 - \xi_1^1}\right) * \left(\frac{\xi^2 - \xi_1^2}{\xi_0^2 - \xi_1^2} * \frac{\xi^2 - \xi_2^2}{\xi_0^2 - \xi_2^2}\right)$$
$$= \frac{1}{4}(\xi^1 + 1^1)(\xi^1)(\xi^2)(\xi^2 - 1)$$

$l_3(0.5, -0.5) = 0.1406$

Lagrange Interpolation Polynomial for reference point 4:

$$l_4(\xi^1, \xi^2) = l_0^2(\xi^1) * l_1^2(\xi^2)$$
$$= \left(\frac{\xi^1 - \xi_1^1}{\xi_0^1 - \xi_1^1} * \frac{\xi^1 - \xi_2^1}{\xi_0^1 - \xi_2^1}\right) * \left(\frac{\xi^2 - \xi_0^2}{\xi_1^2 - \xi_0^2} * \frac{\xi^2 - \xi_2^2}{\xi_1^2 - \xi_2^2}\right)$$
$$= -\frac{1}{2}(\xi^1)(\xi^1 - 1)(\xi^2 + 1)(\xi^2 - 1)$$

$$l_4(0.5, -0.5) = -0.0938$$

Lagrange Interpolation Polynomial for reference point 5:

$$l_5(\xi^1, \xi^2) = l_1^2(\xi^1) * l_1^2(\xi^2)$$
$$= \left(\frac{\xi^1 - \xi_0^1}{\xi_1^1 - \xi_0^1} * \frac{\xi^1 - \xi_2^1}{\xi_1^1 - \xi_2^1}\right) * \left(\frac{\xi^2 - \xi_0^2}{\xi_1^2 - \xi_0^2} * \frac{\xi^2 - \xi_2^2}{\xi_1^2 - \xi_2^2}\right)$$
$$= (\xi^1 + 1)(\xi^1 - 1)(\xi^2 + 1)(\xi^2 - 1)$$

$$l_5(0.5, -0.5) = 0.5625$$

Lagrange Interpolation Polynomial for reference point 6:

$$l_6(\xi^1, \xi^2) = l_2^2(\xi^1) * l_1^2(\xi^2)$$
$$= \left(\frac{\xi^1 - \xi_0^1}{\xi_2^1 - \xi_0^1} * \frac{\xi^1 - \xi_1^1}{\xi_2^1 - \xi_1^1}\right) * \left(\frac{\xi^2 - \xi_0^2}{\xi_1^2 - \xi_0^2} * \frac{\xi^2 - \xi_2^2}{\xi_1^2 - \xi_2^2}\right)$$
$$= -\frac{1}{2}(\xi^1 + 1)(\xi^1)(\xi^2 + 1)(\xi^2 - 1)$$

$$l_6(0.5, -0.5) = 0.2813$$

Lagrange Interpolation Polynomial for reference point 7:

$$l_7(\xi^1, \xi^2) = l_0^2(\xi^1) * l_2^2(\xi^2)$$
$$= \left(\frac{\xi^1 - \xi_1^1}{\xi_0^1 - \xi_1^1} * \frac{\xi^1 - \xi_2^1}{\xi_0^1 - \xi_2^1}\right) * \left(\frac{\xi^2 - \xi_0^2}{\xi_2^2 - \xi_0^2} * \frac{\xi^2 - \xi_1^2}{\xi_2^2 - \xi_1^2}\right)$$
$$= \frac{1}{4}(\xi^1)(\xi^1 - 1)(\xi^2 + 1)(\xi^2)$$

$$l_7(0.5, -0.5) = 0.0156$$

Lagrange Interpolation Polynomial for reference point 8:

$$l_8(\xi^1, \xi^2) = l_1^2(\xi^1) * l_2^2(\xi^2)$$
$$= \left(\frac{\xi^1 - \xi_0^1}{\xi_1^1 - \xi_0^1} * \frac{\xi^1 - \xi_2^1}{\xi_1^1 - \xi_2^1}\right) * \left(\frac{\xi^2 - \xi_0^2}{\xi_2^2 - \xi_0^2} * \frac{\xi^2 - \xi_1^2}{\xi_2^2 - \xi_1^2}\right)$$
$$= -\frac{1}{2}(\xi^1 + 1)(\xi^1 - 1)(\xi^2 + 1)(\xi^2)$$

$$l_8(0.5, -0.5) = -0.0938$$

Lagrange Interpolation Polynomial for reference point 9:

$$l_9(\xi^1, \xi^2) = l_2^2(\xi^1) * l_2^2(\xi^2)$$
$$= \left(\frac{\xi^1 - \xi_0^1}{\xi_2^1 - \xi_0^1} * \frac{\xi^1 - \xi_1^1}{\xi_2^1 - \xi_1^1}\right) * \left(\frac{\xi^2 - \xi_0^2}{\xi_2^2 - \xi_0^2} * \frac{\xi^2 - \xi_1^2}{\xi_2^2 - \xi_1^2}\right)$$
$$= \frac{1}{4}(\xi^1 + 1)(\xi^1)(\xi^2 + 1)(\xi^2)$$

$$l_9(0.5, -0.5) = -0.0469$$

If $w_1=0.0084$, $w_2=0.1972$, $w_3=0.4179$, $w_4=0.1924$, $w_7=0.7359$ and $C=1.5656$, then using equations (9), (10), (11) and (12) $w_5=0.3050$, $w_6=0.4778$, $w_8=0.7304$ and $w_9=0.9032$.

$$\text{Belief value in the cause} = \sum_{i=1}^{9} w_i l_i(0.5, -0.5)$$
$$= 0.3024$$

During a learning or training phase, the predicted belief value (0.3024) is compared with a known belief value in the training data file to calculate the error. Any of the known optimisation method is used to calculate new values of primary weights and coefficients used in the linear combination equations. The new belief value in the cause is again calculated and the process is repeated until a user defined criterion of error minimisation is achieved.

The optimal values of primary weights and coefficients in the linear combination equations are stored and used for future applications.

Embodiments of the present invention has been described above by way of example only and it will be appreciated by a person skilled in the art that modifications and variations can be made to the described embodiments without departing from the scope of the invention.

The invention claimed is:

1. A computer-implemented diagnostic system for determining a likelihood of occurrence of a cause of one or more effects occurring in respect of a subject or process, said one or more effects being input to the system, the system being arranged to receive and/or access training data in the form of discrete values relating to previously-identified relationships between one or more effects and said cause, the system comprising: one or more input nodes arranged to receive respective input signals, the or each input signal being representative of an effect and its relative strength, wherein the number of effects defines the number of dimensional axes of a function representative of said previously-identified relationships; define an input space on the basis of said dimensional axes and select a number of reference points within said input space, a predefined number of said reference points being designated as primary reference points and the rest of said reference points being designated as secondary reference points, said predefined number being dependent on the number of effects associated with said cause in said training data, wherein each reference point has a predetermined weight value assigned thereto, a weight value being representative of a belief value which quantifies the extent of occurrence of said cause given an effect, the weight values assigned to said primary reference points being independent variables ("primary weight") and the weight values assigned to said secondary reference points being dependent on one or more of said primary weights ("secondary weight"), and wherein, in combination, said primary and secondary weights define a multi-dimensional decision hyper-surface representative of said training data; determine, using said decision hyper-surface, a likelihood of occurrence of said cause given said one or more effects input to the system by: receiving input data representative of one or more effects occurring in respect of said subject or process and the relative strength thereof; mapping said input data onto said decision hyper-surface; and determining from said decision hyper-surface a belief value in said cause given said input data and outputting data representative of said determined likelihood of occurrence of said cause to a recipient mechanism for diagnosing a cause of the occurrence of said one or more effects in respect of said subject or process.

2. A computer implemented diagnostic method for determining a likelihood of occurrence of a cause of one or more effects occurring in respect of a subject or process, the method comprising:

receiving and/or accessing training data in the form of discrete values relating to previously-identified relationships between one or more effects and said cause;

providing one or more input nodes arranged to receive respective input signals, the or each input signal being representative of an effect and its relative strength, wherein the number of effects defines the number of dimensional axes of a function representative of said previously-identified relationships;

defining an input space on the basis of said dimensional axes and means for selecting a number of reference points within said input space, a predefined number of said reference points being designated as primary reference points and the rest of said reference points being designated as secondary reference points, said predefined number of primary reference points being dependent on the number of effects associated with said cause in said training data, wherein each reference point has a predetermined weight value assigned thereto, a weight value being representative of a belief value which quantifies the extent of occurrence of said cause given an effect, the weight values assigned to said primary reference points being independent variables ("primary weight") and the weight values assigned to said secondary reference points being dependent on one or more of said primary weights ("secondary weight"), and wherein, in combination, said primary and secondary weights define a multi-dimensional decision hyper-surface representative of said training data;

determining, using said decision hyper-surface, a likelihood of occurrence of said cause given said one or more effects by:

receiving input data representative of one or more effects occurring in respect of said system or process and the relative strength thereof;

mapping said input data onto said decision hyper-surface; and determining from said decision hyper-surface a belief value in said cause given said input data;

and outputting data representative of said determined likelihood of occurrence of said cause to a recipient mechanism for diagnosing a cause of the occurrence of said one or more effects in respect of said subject or process.

3. A system or method according to claim 1 or claim 2, wherein equidistant reference points are selected along each dimension corresponding to each single effect-cause relationship.

4. A system or method according to claim 1 or claim 2, wherein non-equidistant reference points are selected along one or more of said dimensions, and wherein said non-equidistant reference points are mapped onto a set of equidistant reference points.

5. A system or method according to claim 1 or claim 2, wherein primary weight values are assigned to reference points on dimensional axes of said function(s).

6. A system or method according to claim 5, wherein secondary weight values are assigned to reference points in the input space defined by the said dimensions.

7. A system or method according to claim 1 or claim 2, wherein a p-dimensional Lagrange Interpolation polynomial is constructed in respect of each reference point, where p is the number of effects associated with said cause.

8. A system or method according to claim 7, wherein a said Lagrange Interpolation polynomials are combined to construct a multi-dimensional hyper-surface that is representative of said decision hyper-surface.

9. A system or method according to claim 1 or claim 2, wherein a secondary weight value associated with a reference point is a linear combination of those primary weight values, which are associated with primary reference points corresponding to the co-ordinates of the said reference point.

10. A system or method according to claim 1 or claim 2, wherein a secondary weight value associated with a reference point is a constant multiplied by the average of primary weight values, which are associated with primary reference points corresponding to the co-ordinates of the said reference point.

11. A system or method according to claim 1 or claim 2, wherein the training data is made up of one or more training files, the or each file comprising an input vector storing belief values representing strengths of all associated effects and its corresponding desired output vector storing belief values which quantify the extent of occurrence of the corresponding cause.

12. A system or method according to claim 1 or claim 2 wherein optimal values of primary weights and coefficients used in linear combination are determined, during a training or learning process, using an optimization technique involving minimizing the error in the predicted belief value and the corresponding known belief value as given in the training data.

13. A computer-implemented diagnostic system for determining a likelihood of occurrence of a cause of one or more effects occurring in respect of a subject or process, said one or more effects being input to the system, the system being arranged to receive and/or access training data in the form of discrete values relating to previously-identified relationships between one or more effects and said cause, the system comprising:

one or more input nodes arranged to receive respective input signals, the or each input signal being representative of an effect and its relative strength, wherein the number of effects defines the number of dimensional axes of a function representative of said previously-identified relationships;

define an input space on the basis of said dimensional axes and select a number of reference points within said input space, a predefined number of said reference points being designated as primary reference points and the rest of said reference points being designated as secondary reference points, said predefined number of primary reference points dependent on the number of effects associated with said cause in said training data, wherein each reference point has a predetermined weight value assigned thereto, a weight value being representative of a belief value which quantifies the extent of occurrence of said cause given an effect, the weight values assigned to said primary reference points being independent variables ("primary weight") and each weight value ("secondary weight") assigned to respective secondary reference points is expressed as a linear combination of one or more of said primary weights, and wherein, in combination, said primary and secondary weights define a multi-dimensional decision hyper-surface representative of said training data;

determine, using said decision hyper-surface, a likelihood of occurrence of said cause given said one or more effects input to the system by:

receiving input data representative of one or more effects occurring in respect of said subject or process and the relative strength thereof;

mapping said input data onto said decision hyper-surface; and determining from said decision hyper-surface a belief value in said cause given said input data;

and output data representative of said determined likelihood of occurrence of said cause to a recipient mechanism for diagnosing a cause of the occurrence of said one or more effects in respect of said subject or process.

14. A computer-implemented diagnostic method for determining a likelihood of occurrence of a cause of one or more effects occurring in respect of a subject or process, the method comprising:

receiving and/or accessing training data in the form of discrete values relating to previously-identified relationships between one or more effects and said cause;

providing one or more input nodes arranged to receive respective input signals, the or each input signal being representative of an effect and its relative strength, wherein the number of effects defines the number of dimensional axes of a function representative of said previously-identified relationships;

defining an input space on the basis of said dimensional axes and select a number of reference points within said input space, a predefined number of said reference points being designated as primary reference points and the rest of said reference points being designated as secondary reference points, said predefined number of primary reference points dependent on the number of effects associated with said cause in said training data, wherein each reference point has a predetermined weight value assigned thereto, a weight value being representative of a belief value which quantifies the extent of occurrence of said cause given an effect, the weight values assigned to said primary reference points being independent variables ("primary weight") and each weight value ("secondary weight") assigned to respective secondary reference points is expressed as a linear combination of one or more of said primary weights, and wherein, in combination, said primary and secondary weights define a multi-dimensional decision hyper-surface representative of said training data;

determining, using said decision hyper-surface, a likelihood of occurrence of said cause given said one or more given effects by:

receiving input data representative of one or more effects occurring in respect of said subject or process and the relative strength thereof;

mapping said input data onto said decision hyper-surface; and determining from said decision hyper-surface a belief value in said cause given said input data;

and outputting data representative of said determined likelihood of occurrence of said cause to a recipient mechanism for diagnosing a cause of the occurrence of said one or more effects in respect of said subject or process.

15. A computer-implemented diagnostic system for determining a likelihood of occurrence of a cause of one or more effects occurring in respect of a subject or process, said one or more effects being input to the system, the system being arranged to receive and/or access training data in the form of discrete values relating to previously-identified relationships between one or more effects and said cause, the system comprising:

one or more input nodes arranged to receive respective input signals, the or each input signal being representative of an effect and its relative strength, wherein each relative strength value is normalized between 0 and 1 or −1 and 1 and wherein the number of effects defines the number of dimensional axes of a function representative of said previously-identified relationships;

define an input space on the basis of said dimensional axes and select a number of reference points within said input space, a predefined number of said reference points being designated as primary reference points and the rest of said reference points being designated as secondary reference points, said predefined number of primary reference points dependent on the number of effects associated with said cause in said training data, wherein each reference point has a predetermined weight value assigned thereto, a weight value being representative of a belief value which quantifies the extent of occurrence of said cause given an effect, the weight values assigned to said primary reference points being independent variables ("primary weight") and the weight values assigned to said secondary reference points being dependent on one or more of said primary weights ("secondary weight"), and wherein, in combination, said primary and secondary weights define a multi-dimensional decision hyper-surface representative of said training data, said weight values being normalized between 0 and 1 or −1 and 1;

determine, using said decision hyper-surface, a likelihood of occurrence of said cause given said one or more effects input to the system by:

receiving input data representative of one or more effects occurring in respect of said subject or process and the relative strength thereof;

mapping said input data onto said decision hyper-surface; and determining from said decision hyper-surface a belief value in said cause given said input data, said belief value being normalized between 0 and 1 or −1 and 1;

and output data representative of said determined likelihood of occurrence of said cause to a recipient mechanism for diagnosing a cause of the occurrence of said one or more effects in respect of said subject or process.

16. A computer-implemented diagnostic method for determining a likelihood of occurrence of a cause of one or more effects occurring in respect of a subject or process, the method comprising:

receiving and/or accessing training data in the form of discrete values relating to previously-identified relationships between one or more effects and said cause;

providing one or more input nodes arranged to receive respective input signals, the or each input signal being representative of an effect and its relative strength, wherein each relative strength value is normalized between and 1 or −1 and 1 and wherein the number of effects defines the number of dimensional axes of a function representative of said previously-identified relationships;

defining an input space on the basis of said dimensional axes and select a number of reference points within said input space, a predefined number of said reference points being designated as primary reference points and the rest of said reference points being designated as secondary reference points, said predefined number of primary reference points being dependent on the number of effects associated with said cause in said training data, wherein each reference point has a predetermined weight value assigned thereto, a weight value being representative of a belief value which quantifies the extent of occurrence of said cause given an effect, the weight values assigned to said primary reference points being independent variables ("primary weight") and the weight values assigned to said secondary reference points being dependent on one or more of said primary weights ("secondary weight"), and wherein, in combination, said primary and secondary weights define a multi-dimensional decision hyper-surface representative of said training data, said weight values being normalized between 0 and 1 or −1 and 1;

determining, using said decision hyper-surface, a likelihood of occurrence of said cause given said one or more effects by:
receiving input data representative of one or more effects occurring in respect of said subject or process and the relative strength thereof;
mapping said input data onto said decision hyper-surface; and
determining from said decision hyper-surface a belief value in said cause given said input data, said belief value being normalized between 0 and 1 or −1 and 1; and
outputting data representative of said determined likelihood of occurrence of said cause to a recipient mechanism for diagnosing a cause of the occurrence of said one or more effects in respect of said subject or process.

17. A computer-implemented diagnostic system for determining a likelihood of occurrence of an effect of one or more causes occurring in respect of a subject or process, said one or more causes being input to the system, the system being arranged and configured to receive and/or access training data in the form of discrete values relating to previously-identified relationships between one or more causes and said effect, the system comprising:
one or more input nodes arranged to receive respective input signals, the or each input signal being representative of a cause and its relative strength, wherein the number of causes defines the number of dimensional axes of a function representative of said previously-identified relationships;
define an input space on the basis of said dimensional axes and means for selecting a number of reference points within said input space, a predefined number of said reference points being designated as primary reference points and the rest of said reference points being designated as secondary reference points, said predefined number of primary reference points being dependent on the number of causes associated with said effect in said training data, wherein each reference point has a predetermined weight value assigned thereto, a weight value being representative of a belief value which quantifies the extent of occurrence of in said effect given a cause, the weight values assigned to said primary reference points being independent variables ("primary weight") and the weight values assigned to said secondary reference points being dependent on one or more of said primary weights ("secondary weight"), and wherein, in combination, said primary and secondary weights define a multi-dimensional decision hyper-surface representative of said training data;
determine, using said decision hyper-surface, a likelihood of occurrence of said effect given said one or more causes input to the system by:
receiving input data representative of one or more causes occurring in respect of said subject or process and the relative strength thereof;
mapping said input data onto said decision hyper-surface; and
determining from said decision hyper-surface a belief value in said effect given said input data;
and
output data representative of said determined likelihood of occurrence of said effect to a recipient mechanism for diagnosing a cause of the occurrence of said one or more causes in respect of said subject or process.

18. A computer-implemented diagnostic method for determining a likelihood of occurrence of an effect of one or more causes occurring in respect of a subject or process, the method comprising receiving and/or accessing training data in the form of discrete values relating to previously-identified relationships between one or more effects and said cause:
providing one or more input nodes arranged to receive respective input signals, the or each input signal being representative of a cause and its relative strength, wherein the number of causes defines the number of dimensional axes of a function representative of said previously-identified relationships;
defining an input space on the basis of said dimensional axes and selecting a number of reference points within said input space, a predefined number of said reference points being designated as primary reference points and the rest of said reference points being designated as secondary reference points, said predefined number of primary reference points being dependent on the number of causes associated with said effect in said training data, wherein each reference point has a predetermined weight value assigned thereto, a weight value being representative of a belief value which quantifies the extent of occurrence of said effect given a cause, the weight values assigned to said primary reference points being independent variables ("primary weight") and the weight values assigned to said secondary reference points being dependent on one or more of said primary weights ("secondary weight"), and wherein, in combination, said primary and secondary weights define a multi-dimensional decision hyper-surface representative of said training data;
determining, using said decision hyper-surface, a likelihood of occurrence of said effect given said one or more causes by:
receiving input data representative of one or more causes occurring in the subject or process and the relative strength thereof;
mapping said input data onto said decision hyper-surface; and determining from said decision hyper-surface a belief value in said cause given said input data;

and outputting data representative of said determined likelihood of occurrence of said effect to a recipient mechanism for diagnosing an effect of the occurrence of said one or more causes in respect of said subject or process.

19. A computer-implemented diagnostic system for determining a likelihood of occurrence of a medical condition (cause) of one or more manifestations of the medical condition occurring in respect of a subject or process, said one or more manifestations being input to the system, the system being arranged to receive and/or access training data in the form of discrete values relating to previously-identified relationships between one or more manifestations and said cause, the system comprising:

one or more input nodes arranged to receive respective input signals, the or each input signal being representative of a manifestation and its relative strength, wherein the number of manifestations defines the number of dimensional axes of a function representative of said previously-identified relationships;

define an input space on the basis of said dimensional axes and select a number of reference points within said input space, a predefined number of said reference points being designated as primary reference points and the rest of said reference points being designated as secondary reference points, said predefined number being dependent on the number of manifestations associated with said cause in said training data, wherein each reference point has a predetermined weight value assigned thereto, a weight value being representative of a belief value which quantifies the extent of occurrence of said cause given a manifestation, the weight values assigned to said primary reference points being independent variables ("primary weight") and the weight values assigned to said secondary reference points being dependent on one or more of said primary weights ("secondary weight"), and wherein, in combination, said primary and secondary weights define a multi-dimensional decision hyper-surface representative of said training data;

determine, using said decision hyper-surface, a likelihood of occurrence of said cause given said one or more manifestations input to the system by:

receiving input data representative of one or more manifestations occurring in respect of said subject or process and the relative strength thereof;

mapping said input data onto said decision hyper-surface; and determining from said decision hyper-surface a belief value in said cause given said input data;

and outputting data representative of said determined likelihood of occurrence of said cause to a recipient mechanism for diagnosing a cause of the occurrence of said one or more manifestations in respect of said subject or process.

* * * * *